United States Patent
Marraccini et al.

(10) Patent No.: US 7,238,858 B2
(45) Date of Patent: Jul. 3, 2007

(54) COFFEE PLANT WITH REDUCED α-D-GALACTOSIDASE ACTIVITY

(75) Inventors: Pierre Marraccini, Paraná (BR); Alain François Paul Edmond Deshayes, Saint Cyr sur Loire (FR); William John Rogers, St Jean-de-Gonville (FR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 10/804,096

(22) Filed: Mar. 19, 2004

(65) Prior Publication Data

US 2004/0199943 A1    Oct. 7, 2004

Related U.S. Application Data

(63) Continuation of application No. PCT/EP02/09148, filed on Aug. 15, 2002.

(30) Foreign Application Priority Data

Oct. 10, 2001    (EP)    ................... 01124160

(51) Int. Cl.
| | |
|---|---|
| C12N 15/82 | (2006.01) |
| C12N 5/04 | (2006.01) |
| C12N 5/10 | (2006.01) |
| A01H 5/00 | (2006.01) |
| A01H 5/10 | (2006.01) |
| C12N 15/29 | (2006.01) |
| C12N 15/56 | (2006.01) |

(52) U.S. Cl. .................. 800/284; 800/286; 435/208; 435/419

(58) Field of Classification Search ............. 800/455; 546/23.6; 435/278
See application file for complete search history.

(56) References Cited

U.S. PATENT DOCUMENTS 6,329,191 B1    12/2001    Ivy et al. ............ 435/240.1
2003/0131380 A1    7/2003    Marraccini et al. ........ 800/284

FOREIGN PATENT DOCUMENTS

EP    1 138 771 A1    10/2001
WO    WO 95/06478    3/1995

OTHER PUBLICATIONS

Shen et al. Eur. J. Biochem. 268, p. 2331-2337. 2001.*
Willmitzer etal. Starch synthesis in transgenic pants. In Plant polymeric carbohydrates. International symposium. Meuser et al (Eds). Berlin, Germany. Royal Society of Chemistry: Cambridge, England, UK. Jul. 1-3. 1993. p. 33-39.*
Kull et al. J. Genet. & Breed. 49(1). p. 69-76. 1995.*
Colliver et al. Plant Molecular Biology 35: 509-522 (1997).*
A. Zhu et al., XP0020621, "Cloning And Functional Expression Of A CDNA Encoding Coffee Bean *Alpha—Galactosidase*", Gene, Elsevier Biomedical Press. Amsterdam, NL, vol. 140, No. 2, pp. 227-231 (1994).
K. Golden et al., XP008002908, "Beta—Galactosidase from Coffea arabica and its role in fruit ripening", Phytochemistry (Oxford), vol. 34, No. 2, pp. 355-360, (1993).
J. M. Cock et al., XP002252703, "Natural antisense transcripts of the S locus receptor kinase gene and related sequences in *Brassica oleracea.*", Molecular & General Genetics, vol. 255, No. 5, pp. 514-524, (1997).
Pierre Marraccini et al., XP002197483 "Molecular cloning of the complete11S seed storage protein gene of Coffea arabica and promoter analysis in transgenic tobacco plants" Plant Physiology And Biochemistry (Paris), vol. 37, No. 4, pp. 273-282 (1999).
A. Sachslehner et al., XP004213502, "Hydrolysis of isolated coffee mannan and coffee extract by mannanases of *Sclerotium rolfsii*" Journal Of Biotechnology, Elsevier Science, Publishers, Amsterdam, NL, vol. 80, No. 2, pp. 127-134 (2000).
F. Haibach et al., XP000644469, "Purification And Characterization Of A Coffea Canephora Alpha—D—Galaciosidase Isozyme" Biochemical And Biophysical Research Communications, Academic Press Inc.Orlando, Fl, US, vol. 181, No. 3, pp. 1564-1571, (1991).

* cited by examiner

*Primary Examiner*—David T. Fox
(74) *Attorney, Agent, or Firm*—Bell, Boyd & Lloyd LLP

(57) ABSTRACT

The present invention relates to the modification of galactomannans present in the green coffee bean by reducing the endogenous level of α-D-galactosidase activity. In particular, the present invention pertains to a plant cell with reduced α-D-galactosidase activity and to a plant harboring such a plant cell.

7 Claims, No Drawings

COFFEE PLANT WITH REDUCED α-D-GALACTOSIDASE ACTIVITY

CROSS-REFERENCE TO RELATED APPLICATIONS

This application is a continuation of International application PCT/EP02/09148 filed Aug. 15, 2002, the entire content of which is expressly incorporated herein by reference thereto.

BACKGROUND ART

The present invention relates to the modification of galactomannans present in green coffee beans by reducing the endogenous level of α-D-galactosidase activity. In particular the present invention pertains to a plant cell having a reduced α-D-galactosidase activity and to a plant harboring such a plant cell.

In coffee grains, cell wall polysaccharides account for approximately 48% of mature coffee bean dry weight, and of these, mannans represent approximately half. These polysaccharides are essentially insoluble in purified form and have very low galactose branching (Bradbury and Haliday, J. agric. Food Chem. 38 (1990), 389–392). Mannan polymers are acknowledged to be the main reason for the large losses of original green coffee weight encountered during preparation of soluble coffee drinks. The losses occur either when insoluble material remains as sediments during initial extraction or when precipitates and gels form during storage of coffee liquors. Mannans have also been shown to be the principal component responsible for cloudiness and precipitation during standing of coffee beverages.

In some plants, the degree of galactose branching on the mannan chains has been found to partially depend on the activity of the α-D-galactosidase (EC 3.2.1.22). This enzyme is capable of releasing α-1,6-linked galactose units from galactomannans stored in plant seed storage tissue or maturation (Buckeridge and Dietrich, Plant Sci. 117 (1996), 33–43). In addition, the accumulation of galactomannans having a very low galactose/mannose ratio in some plant endosperms or cotyledon tissues has been shown to correlate to peak α-D-galactosidase activity during maturation of these tissues and to the hardening and drying thereof (Kontos and Spyropoulos, Plant Physiol. Biochem. 34 (1996), 787–793).

α-D-galatosidases activity has also been associated with the capacity to remove galactose residues, i.e., α-1,6-linked to galactomannan polysaccharides, which brings about a decreased solubility of these polymers (McCleary, Carb. Res. 92 (1981), 269–285). Furthermore, the removal of galactose side chains from galactomannans seems to increase the capacity thereof to interact with other polysaccharides, e.g., xanthans in guar, with a concomitant formation of complex gel. Galactose branching on coffee grain mannans decreases from approximately 40% in young grains to the low level found in the mature grains during maturation. Concurrently, α-D-galactosidase enzyme activity increases during coffee grain maturation.

The coffee α-D-galactosidase cDNA has been cloned (Zhu and Goldstein, Gene 140 (1994), 227–231). According to the information derived therefrom, the mature coffee bean α-D-galactosidase is presumed to be composed of 363 amino acids and is synthesized as a pre-proenzyme of 420 residues. Following biosynthesis, two protease cleavages then remove a secretion signal (38 residues) and another signal peptide (19 residues) to produce the protein exhibiting the N-terminal amino acid sequence characteristic of the active enzyme.

In view of the known effects of galactomannans on the preparation and/or storability of soluble coffee, there is a need in the art to improve this situation. More specifically, there is a need to provide an improved method for preparing soluble coffee while concurrently obviating the drawbacks known when storing coffee liquors.

SUMMARY OF THE INVENTION

The present invention satisfies the above-mentioned needs by providing a coffee plant cell, and a coffee plant, respectively, wherein the galactose branching in the galactomannans is increased. The increased galactose branching is in turn achieved by reducing the endogenous level of α-D-galactosidase activity.

The coffee plant cell generally contains a nucleic acid that is transcribed to a ribonucleic acid which is antisense to mRNA, or a part thereof, derived from the α-D-galactosidase gene of the cell. Advantageously, the nucleic acid is under the control of a constitutive or inducible promoter, such as a coffee csp1 promoter.

The invention also relates to a coffee plant containing a coffee plant cell as described herein. This plant can produce coffee beans which form yet another embodiment of the invention. These coffee beans can be used in a method for preparing a coffee beverage or a method for increasing the solubility of coffee particles

DETAILED DESCRIPTION OF THE PREFERRED EMBODIMENTS

According to a preferred embodiment of the invention, a coffee plant cell, and a coffee plant, respectively, may be obtained by reducing the endogenous level of α-D-galactosidase activity so that the galactose branching in the galacto-mannans is increased. The reduction of α-D-galactosidase activity may be achieved by conventional methods of mutation and selection using the techniques available in the art. Thus, plant cells may be subjected to mutagenic treatments, such as by exposing them to chemicals or radiation that bring about an alteration of the cell's DNA. The cells thus treated are subsequently screened for the desired property.

According to another preferred embodiment, such a reduced endogenous level of α-D-galactosidase activity is obtained by introducing a construct into a coffee plant cell, containing a nucleic acid that is transcribed into an antisense copy of the mRNA encoded by the α-D-galactosidase gene, or to a part thereof.

To this end, the antisense copy of the mRNA encoded by the α-D-galactosidase gene may be any ribonucleic acid capable of forming dimers under physiological conditions, i.e., to hybridize with the mRNA encoded by the α-D-galactosidase gene under conditions prevailing in the cell. Thus, the antisense copy does not need to be a 100% homologue to the corresponding counterpart, but rather needs to provide sufficient binding for forming a dimer. Consequently, antisense copies (and the corresponding nucleic acids from which they are transcribed), that are modified by substitution, deletion and/or insertion of nucleotides are well within the context of the present invention. In this respect, it will also be appreciated that the antisense copy may represent a full counterpart to the mRNA encoded by the α-D-galactosidase gene, that is, it may provide a RNA molecule having essentially the same length as the mRNA encoding the α-D-galactosidase polypeptide. On the other hand the antisense copy may only cover a part of the mRNA encoding the α-D-galactosidase polypeptide.

The nucleic acid encoding a ribonucleic acid, antisense to the mRNA encoded by the α-D-galactosidase gene, or to a part thereof, may be under the control of a constitutive or an inducible promoter, so that the level of the antisense RNA may be conveniently controlled. However, in all cases the level of the antisense copy should be sufficiently high so as to reduce the number of mRNA copies encoding the α-D-galactosidase polypeptide accessible for the ribosomes.

According to a preferred embodiment the promoter utilized is the coffee csp1 promoter, which gives a sufficiently high transcription rate.

The present invention therefore provides for a modified coffee plant cell and a coffee plant, respectively, wherein the level of α-D-galactosidase activity has been reduced such that eventually the galactose branching on galacto-mannans is increased. According to a preferred embodiment the plant is a transgenic plant, the cells of which harbor a construct capable to provide an antisense copy of the mRNA derived from the α-D-galactosidase gene or a part thereof.

The present invention also provides a method for preparing soluble coffee, which comprises the step of using coffee beans derived from a plant exhibiting a reduced α-D-galactosidase activity. In this respect the present invention also provides a method for increasing the solubility of coffee by increasing the galactose branching.

This invention aims to increase in the solubility of coffee galacto-mannans by increasing their galactose branching. The strategy adopted is to reduce the endogenous level of α-D-galactosidase activity, preferably by introducing an antisense copy of its cDNA under the control of the coffee csp1 promoter.

This csp1 promoter has already been characterized (Marraccini et al., Plant Physiol. Biochem. 37 (1999), 273–282) and controls the expression a gene encoding coffee 11S storage protein. A cassette containing said promoter was constructed and introduced into the T-DNA region of a binary vector of transformation, which derives from the pTiT37 plasmid (Bevan, Nucl. Acids Res. 12 (1984), 8711–8721). This recombinant vector was introduced in *Agrobacterium tumefaciens*, which was used to transform coffee explants. Coffee plants harboring the T-DNA inserted in their genome were regenerated and analyzed for the α-D-galactosidase activity in their grains.

I. Analysis of the α-D-Galactosidase Activity in Coffee Grains During Maturation Fruits were harvested at different stage of maturation (age is expressed as weeks after flowering: WAF) from *Coffea arabica* variety Caturra T2308 grown in greenhouse (temperature of approximately 25° C., 70% humidity and natural lighting). Cherries were frozen in liquid nitrogen subsequent to harvesting and stored at −85° C. until use. For maturation studies, endosperm and perisperm tissues were separated.

Plant material was ground in liquid nitrogen and extracted in ice cold enzyme extraction buffer (glycerol 10% v/v, sodium metabisulfite 10 mM, EDTA 5 mM, MOPS (NaOH) 40 mM, pH 6.5) at an approximate ratio of 20 mg per 100 µl. The mixture was stirred on ice for 20 min, subjected to centrifugation (12,000 g×30 min), aliquoted and stored at −85° C. until use. α-D-galactosidase activity was detected spectrophotometrically with the substrate p-nitrophenyl-α-D-galactopyranoside (pNGP).

The reaction mixture contained 200 µl pNGP 100 mM in McIlvain's buffer (citric acid 100 mM—$Na_2HPO_4$ 200 mM pH 6.5) up to final volume of 1 ml with enzyme extract. The reaction was maintained at 26° C. and started with the addition of enzyme and was stopped by addition of 4 volumes of stop solution ($Na_2CO_3$—$NaHCO_3$ 100 mM pH 10.2). Absorption is read at 405 nm. Evolution of nitrophenyl is calculated using molar extinction coefficient $\epsilon=18300$ (specific for pH 10.2) and converted to mmol $min^{-1}$ mg $protein^{-1}$. Total protein was measured in samples extracted in aqueous buffers by the method of Bradford (Anal. Biochem., 72 (1976), 248–254). For the expression of activity, each sample was extracted and aliquoted, and assays were performed in triplicate, the results being expressed as averages.

α-D-galactosidase activity is extremely low or undetected in the young grain stages, and reaches a peak that coincides with a reddening of color of the pericarp. In later stages the activity declines while the cherries are still red. Activities are also compared in different tissues of coffee plant. The activity in perisperm, roots and leaves is particularly low, and close to the limits of detection. However, high activities are recorded in the endosperm where the activity reaches a peak at approximately 36 WAF but also in germinating grain following imbibition of water.

II. Isolation of α-D-galactosidase Full-length cDNA from *C. arabica*

Though several coffee α-D-galactosidase cDNA sequences are available in the literature the origin of the coffee material is not indicated. In order see if amino acid and nucleic sequence differences are observed between *C. arabica* and *C. canephora*, it was decided to clone α-D-galactosidase cDNAs from both species.

A cDNA library from *Coffea arabica* var. *Caturra* T2308 was constructed with polyA+ mRNA extracted at 30 weeks after flowering according to Rogers et al. (Plant Physiol. Biochem., 37 (1999), 261–272). This plasmid cDNA library (10 ng) was tested by PCR using the primers BETA1 (SEQ ID NO: 3) and BETA3 (SEQ ID NO: 4) directly deduced from the coffee α-D-galactosidase cDNA sequence (Zhu and Goldstein, 1994). The BETA1 primer is located between the nucleotides 177 and 193 in the sequence SEQ ID NO: 1. The BETA3 primer is located between the nucleotides 1297 and 1313 in the sequence SEQ ID NO: 1. The PCR reaction was performed with Pfu DNA polymerase (Stratagene, 11011 North Torrey Pines Road, La Jolla, Calif. 92037, USA) in appropriate 1× Buffer, 0.2 mM of each dNTP and 0.25 µM of each oligonucleotides. Denaturation, annealing and extension temperatures are 94° C. for 30s, 46° C. for 30s and 72° C. for 3 min, respectively. This cycle was repeated 30 times in Robocycler Statagene (USA). PCR products were purified with a Microcon 100 (Millipore SA, BP307 Saint Quentin Yvelines cedex 78054, France) cartridge and ligated in the pCR-Script SK (+) as described by Stratagene (USA). The ligation mixture was then used to transform *E. coli* strain XL1-Blue MRF' and a recombinant vector containing the α-D-galactosidase fragment was purified and cloned into the SfrI site of the pCR-Script SK Amp (+). Its sequence is located between the positions 177 and 1313 of the sequence SEQ ID NO: 1.

According to literature, the 5' end of the α-D-galactosidase cDNA contains 198 bp upstream the 5' end of the BETA 1 primer. In order to clone this sequence from our genotype, we perform an additional PCR, as described previously, with the primers BETA100 (SEQ ID NO: 5) and BETA101 (SEQ ID NO: 6). This *C. arabica* sequence was cloned into the pCR Script Amp SK (+) vector to give the pLP1, and corresponds to SEQ ID NO: 1.

The cDNA obtained contains an open reading frame of 1263 bp, beginning in position 51 and ending in position 1313 of the sequence SEQ ID NO: 1. The translation product corresponds to sequence SEQ ID NO: 2 suggesting that the coffee α-D-galactosidase is synthesized as a preproenzyme, using the translational start codon ATG in position 51 instead of the ATG in position 126. On the other hand, the analysis of the α-D-galactosidase cDNA cloned from *C. canephora* showed that its translation product is very homologous (similarity >99%) to the protein found in *C. arabica*.

III. Expression of α-D-galactosidase Gene During Grain Maturation

The expression of the gene encoding the α-galactosidase in coffee beans of *C. arabica Caturra* harvested at various stages of development, i.e., 9, 12, 16, 30 and 35 weeks after flowering (WAF) was monitored. To do this, 10 μg of total RNAs of these coffee beans were denatured for 15 min at 65° C. in 1×MOPS buffer (20 mM MOPS, 5 mM sodium acetate, 1 mM EDTA, pH 7) in the presence of formamide (50%) and formaldehyde (0.66 M final). They were then separated by electrophoresis, for 6 hrs at 2.5 V/cm, in the presence of 1×MOPS buffer, on a 1.2-% agarose gel containing 2.2 M formaldehyde as final concentration.

After migration, the RNAs were stained with ethidium bromide (BET) according to Sambrook et al. (Molecular Cloning, A Laboratory Manual, Cold Spring Harbor Laboratory Press, USA, 1989, chapter 9.31 to 9.51). This makes it possible to standardize the quantities deposited on a gel from the intensities of fluorescence of the 18S and 25S ribosomal RNAs. The total RNAs were then transferred and fixed on a positively charged Nylon membrane according to the recommendations provided by Boehringer Mannheim (Roche-Boehringer Mannheim GmbH, Biochemica, Postfach 310120, Mannheim 31, DE). The pre-hybridization and hybridization were carried out according to the conditions described above.

Results from Northern-blotting demonstrated a peak of gene expression during the early phase of endosperm development. The peak of specific mRNA expression under greenhouse conditions occurred at approximately 26 WAF, and corresponds to the start of increase in enzyme activity. The peak period of mRNA expression corresponds to the major period of endosperm expansion and hardening taking place in the maturing grains under these conditions. Peak expression for α-galactosidase-specific mRNA either coincided or was slightly later than peak expression of the 11S grain storage protein mRNA. These results led to the construction of an antisense cassette of the coffee cDNA encoding for the α-galactosidase, under the control of the 11S-coffee promoter, in order to reduce the level of α-galactosidase activity in coffee grains under maturation.

IV. Construction of the α-galactosidase Antisense Cassette

The 11S promoter sequence (Marraccini et al., Plant Physiol. Biochem. 37 (1999), 273–282) from coffee is amplified with the specific primers UP210-1 corresponding to the sequence SEQ ID NO: 7, and BAGUS2, corresponding to the sequence SEQ ID NO: 8. The oligonucleotide UP210-1 corresponds to the sequence between the nucleotides 24 and 76 published by Marraccini et al., supra and contains within its 5' end the synthetic sequence CGGGG-TACCCCG containing a KpnI restriction site and corresponding to the sequence SEQ ID NO: 9. The BAGUS2 primer contains in its 5' end the synthetic sequence CGCG-GATCCGCG corresponding to the sequence SEQ ID NO: 10 which carries a BamHI restriction site. This primer also contains the nucleotides 998 to 976 of the sequence published by Marraccini et al. (1999). This reaction is carried out in the presence of Pfu DNA polymerase (3 units), with 10 ng of pCSPP4 (WO 99/02688), in a final volume of 50 μl containing 10 mM KCl, 6 mM (NH$_4$)$_2$SO$_4$, 20 mM Tris-HCl, pH 8.0, 0.1% Triton X-100, 2 mM MgCl$_2$, 10 μg/ml BSA, 0.2 mM of each dNTP, 0.25 μM of each oligonucleotides described above. The reaction mixture was then incubated for 30 cycles (94° C.-60 s, 55° C.-60s, 72° C.-3 min) followed by a final extension cycle at 72° C. for 7 min.

The PCR fragment of about 950 bp was purified on a Microcon 100 cartridge (Millipore, France), and ligated in the pCR-Script Amp SK (+) vector in the presence of T4 DNA ligase (Promega Corporation, 2800 Woods Hollow Road, Madison, Wis. 53711 USA), according to the recommendations provided by the supplier. Next, the *E. coli* strain XL1-Blue MRF' was transformed with the entire ligation mixture. One transformant was selected and its plasmid was purified to sequence the insert in order to determine the orientation of the PCR fragment. This analysis thus made it possible to select the plasmid pLP7.

A shorter version of the 11S promoter was also amplified by the same approach except that the primer UP213-1, having the nucleic sequence SEQ ID NO: 11 replaces the primer UP210-1. This primer corresponds to the sequence between the nucleotides 754 and 777 published by Marraccini et al., supra, and contains in its 5' end the synthetic sequence SEQ ID NO: 9. This led to the amplification of a 250 bp fragment of the p11S coffee promoter which was cloned as described previously to give the plasmid pLP8.

The TNOS terminator is amplified following the protocol described for the amplification of the p11S promoter excepted that the primers TNOS1, having the nucleic sequence SEQ ID NO: 12 and TNOS2, having the nucleic sequence SEQ ID NO: 13 were used. TNOS1 contains the sequence SEQ ID NO: 10 in its 5' end. TNOS2 contains the sequence SEQ ID NO: 9 in its 5' end sequence. These primers led to the amplification of the TNOS sequence from the p35SGFP commercial vector (Clontech Laboratories Inc., 1020 East Meadow Circle, Palo Alto, Calif. 94303–4230 USA). The PCR product was cloned in the pCR-Script Amp SK (+) vector as described before, leading to the recombinant vector called pLP32 and was sequenced to determine its orientation. This vector was then digested by BamHI to remove the TNOS sequence that was treated afterwards by the T4 DNA polymerase to provide blunt ends.

In the other hand, the pLP7 and pLP8 vectors were linearized by EcoRI and also treated with T4 DNA polymerase to provide blunt ends. The TNOS terminator was then cloned in the correct orientation in the pLP7 and pLP8 vectors leading to the vectors p11STNOS7 and p11STNOS7+, respectively.

The α-galactosidase cDNA was amplified from the previously isolated vector pLP1, using the conditions described above except that the primers BETA100B1, having the nucleic sequence SEQ ID NO: 14 and BETA101B1, having the nucleic sequence SEQ ID NO: 15 were used. These oligonucleotides correspond to the previously used BETA101 and BETA100 primers in which a BamHI restriction site, corresponding to the sequence SEQ ID NO: 10, has been introduced in their 5' ends. The PCR product was cloned into the pCR-Script Amp SK (+) vector as described before, leading to the recombinant vector called pLP20.

This plasmid was digested with BamHI to release the α-galactosidase cDNA. On the other side, recipient vectors p11STNOS7 and p11STNOS7+ were digested independently by means of the same restriction enzyme and dephosphorylated by a CIAP treatment according to the furnisher (Promega, USA). The α-galactosidase cDNA was cloned in the antisense orientation, respectively in the p11STNOS7 and p11STNOS7+ vectors, leading to the vectors designated pALPHA1 and pALPHA9.

To mobilize these cassettes into the binary vector used during the transformation of coffee cell suspension, a final PCR reaction with the Pfu DNA polymerase was carried out using the primers UPSAL1, having the nucleic sequence SEQ ID NO: 16 and UPSAL2, having the nucleic sequence SEQ ID NO: 17. Both oligonucleotides contain a SalI restriction site and recognize DNA sequences of the pCR Script Amp SK (+) vector flanking the 11S promoter and the NOS terminator (TNOS) DNA regions. In addition this restriction site is absent from the sequence which was intended to be introduced into the T-DNA of the binary plasmid. These PCR products were cloned again into the pCR-Script Amp SK (+) vector, which was digested with SalI to verify that this restriction site flanks the cassettes. Plasmids obtained were called pALP414 and pALP50, and derive respectively from pALPHA1 and pALPHA9.

V. Cloning of the α-galactosidase Antisense Cassette in the Binary Vector of Transformation The α-galactosidase cassettes contained in the vectors pALP414 and pALP50 were sequenced to verify their integrity, particularly to confirm that no point mutations or rearrangements have occurred during the PCR amplification cycles. These cassettes were then purified by digestion of the pALP414 and pALP50 vectors with the SalI restriction enzyme and cloned independently into the pBin19 derivative plasmid related to the vector described by Leroy et al. (Plant Cell Rep. 19 (1999), 382–389), except that the gene crylAc was absent. In order to do this, the vector was digested with the SalI restriction enzyme, which recognizes a unique site between the uidA and csr1-1 genes, and was dephosphorylated. After this ligation, the vectors pBIA121, pBIA126 and pBIA9 were selected. In the pBIA121 vector, the SalI cassette obtained from pALP414 is cloned in the orientation [LB] Gus-intron>p11S (long) antisense α-galactosidase cDNA>csr1-1 [RB]. However, the same cassette is cloned in the reverse orientation in the pBIA126 vector. In the other hand, the SalI cassette obtained from pALP50 cloned in the pBIA9 vector is in the following orientation: [LB] Gus-intron>p11S (short) antisense α-galactosidase cDNA>csr1-1 [RB].

VI. Transformation of *Agrobacterium tumefaciens*

The binary vectors of transformation pBIA121, pBIA126 and pBIA9 described above were introduced independently into the disarmed *Agrobacterium tumefaciens* strain LBA4404 according to the direct transformation method described by An et al. (Plant Mol. Biol. Manuel, Gelvin, Schilperoort and Verma Eds, Kluwer Academic Publishers Dordrecht, Netherlands, A3 (1993), 1–19). For each transformation, the recombinant *Agrobacterium tumefaciens* clones were selected on LB medium supplemented with kanamycin (50 µg/ml), stretomycin (100 µg/ml) and rifampicin (50 µg/ml).

In order to check the structure of the plasmids introduced into *Agrobacterium tumefaciens*, they were extracted by the rapid mini-preparation technique and were then analyzed by restriction mapping after reverse transformation in *E. coli* strain XL2 Blue MRF'.

VII. Transformation of *Coffea* sp.

Leaf explants were cultured and subcultured every five weeks for 3 to 5 months until somatic embryos appeared at the edge o the explants. Somatic embryos were harvested at the torpedo stage, wounded with a sterile scalpel and soaked for two hours in a 0.9% NaCl solution containing recombinant *Agrobacterium tumefaciens* strain LBA4404 at a $OD_{600nm}$ of 0.3 to 0.5. The co-culture was performed in the dark on semi-solid MS medium without hormones during three days and then washed in liquid MS medium containing cefotaxim (1gr/1) for 3 to 5 hours under constant but gentle agitation. Embryos were cultivated on semi-solid medium with 5 µM of BAP, 90 µM sucrose in presence of cefotaxim (400 mg/l) under low-light condition (16 hrs photoperiod per day). After a period of 3 to 4 weeks, they were transferred to a selective MS medium supplemented with cefotaxim (400 mg/l) and chlorsulfuron (80 mg/l). They were then transferred every month to a new selective medium until the regeneration of calli. Transformed embryos growing around the calli were then cultured on the semi-solid MS medium with Morel vitamins (1 µM BAP and 30 µM sucrose) to induce their germination. After this step, they were transferred on the rooting medium corresponding to the medium described before but without BAP.

To check the effectiveness of the transformation, calli, shoots, roots and leaves were regularly tested for the expression of the uidA reporter by a GUS histochemical assay (Jefferson et al., J. EMBO 6 (1987), 3901–3907).

After this procedure, several individual plants were selected and propagated in vitro by micro cuttings. Some of them were transferred in greenhouse to achieve their development. No morphological anomalies were observed.

VIII. Analysis of Somatic Embryos from Transformed Coffee Plants

Somatic embryos were also induced from leaf explants to detect the presence of α-galactosidase antisense mRNA. 11S coffee storage proteins were detected in somatic embryos (Yuffa et al., Plant Cell Rep. 13 (1994) 197–202), suggesting that the csp1 promoter is active in this tissue. If this is the case, analysis of somatic embryos induced from leaves of young transgenic coffee plants should permit to detect the presence of the α-galactosidase antisense mRNA earlier than in beans.

Total RNAs were then extracted from 100 mg of transformed somatic embryos as described previously and tested by RT-PCR using the kit Access RT-PCR system (Promega, USA). Firstly the presence of 11S specific mRNA was confirmed by performing a RT-PCR using the primers located in the coding sequence of the 11S cDNA. This was performed using the primers SO11 corresponding to the sequence SEQ ID NO: 18 and $SO_2$-1 corresponding to the sequence SEQ ID NO: 19. The SO11 primer corresponds to the sequence between the nucleotides 1035 and 1059 of the sequence published by Marraccini et al., supra. On the other hand, the SO2-1 primer corresponds to the last 24 nucleotides of the sequence published. The synthesis of the first strand of the cDNA (step of reverse transcription) was performed as described by the furnisher (45 min., 48° C.). The following parameters were used for the PCR reaction: 45 cycles (60 sec. at 94° C. for the denaturation step, 90 sec at 52° C. for the annealing step, 4 min at 68° C. for the elongation step) with a final extension at 68° C. for 7 min.

From this experiment a PCR product of 1590 bp corresponding to the 11S cDNA sequence flanked by the primers SO11 and SO2-1 was obtained. The result confirmed that 11S mRNA were absent from all the tissue tested, i.e. roots, leaves, flowers but were effectively present in somatic embryos of *Coffea canephora* as well as in beans at 27 WAF.

Secondly, the presence of the α-galactosidase sense mRNA was tested by performing a RT-PCR reaction using only the primer B33, corresponding to the sequence SEQ ID NO: 21 during the phase of reverse transcription (condition 1). This primer corresponds to the complementary sequence of the nucleotides 1286 to 1314 of the sequence SEQ ID NO: 1.

In parallel, the detection of the α-galactosidase antisense mRNA was performed using only the primer B11 during the phase of reverse transcription (condition 2). This primer corresponds to the sequence between the nucleotides 50 and 78 of the sequence SEQ ID NO: 1. After this reverse transcription (45 min., 48° C.), the reaction mixture was treated at 94° C. during 1 min to inactivate the MMLV reverse transcriptase. The missing oligonucleotide, B11 in the condition 1 and B33 in condition 2, was added and the reaction was continued by a PCR: 45 cycles (60 sec. at 94° C. for the denaturation step, 90 sec at 45° C. for the annealing step, 4 min at 68° C. for the elongation step) with a final extension at 68° C. for 7 min. Using somatic cells from non transformed *C. arabica*, an amplification product of 1310 bp was observed for the condition 1 but not for the condition 2 experiment. However, for somatic embryos obtained from a coffee plantlet transformed by the pBIA9 vector, it was possible to detect an amplification product during the experimental condition 2, confirming the presence of the α-galactosidase anti sense mRNA.

What is claimed is:

1. A coffee plant cell that produces galacto-mannans and that is modified to reduce endogenous levels of alpha-D-galactosidase mRNA, wherein the coffee plant cell comprises an antisense cassette comprising a full-length alpha-D-galactosidase coding sequence from coffee operably linked to a promoter in antisense orientation.

2. The coffee plant cell according to claim 1, wherein the promoter is a constitutive or inducible promoter.

3. The coffee plant cell according to claim 2, wherein the promoter is a coffee csp1 promoter.

4. A coffee plant containing a coffee plant cell according to claim 1.

5. Coffee beans obtained from the coffee plant according to claim 4, wherein said beans comprise said antisense cassette.

6. The coffee beans of claim 5 having increased water solubility compared to conventional coffee beans.

7. A coffee bean comprising a cell that produces galacto-mannans that is modified to reduce endogenous levels of alpha-D-galactosidase mRNA, wherein the coffee plant cell is produced according to the method of claim 1.

* * * * *

SEQUENCE LISTING

```
<160> NUMBER OF SEQ ID NOS: 21

<210> SEQ ID NO 1
<211> LENGTH: 1442
<212> TYPE: DNA
<213> ORGANISM: coffee arabica

<400> SEQUENCE: 1
tgctccacaa agcagtggca attgagttga ttgatcaaca ccaatttacc atggccgctg      60
cttattacta ccttttttct agtaaaaaaa gccaccaaaa gctggtgctc cgagcttcgt     120
tattgatgtt tttatgtttc ttggcggttg aaaacgttgg tgcttccgct cgccggatgg     180
tgaagtctcc aggaacagag gattacactc gcaggagcct tttagcaaat gggcttggtc     240
taacaccacc gatgggtgg aacagctgga atcatttcag ttgtaatctt gatgagaaat      300
tgatcaggga aacagccgat gcaatggcat caaaggggct tgctgcactg ggatataagt     360
acatcaatct tgatgactgt tgggcagaac ttaacagaga ttcacagggg aatttggttc     420
ctaaaggttc aacattccca tcagggatca aagccttagc agattatgtt cacagcaaag     480
gcctaaagct tggaatttac tctgatgctg gaactcagac atgtagtaaa actatgccag     540
gttcattagg acacgaagaa caagatgcca aaaccttttgc ttcatggggg gttgattact     600
taaagtatga caactgtaac gacaacaaca taagccccaa ggaaaggtat ccaatcatga     660
gtaaagcatt gttgaactct ggaaggtcca tattttctc tctatgtgaa tggggagatg     720
aagatccagc aacatgggca aaagaagttg gaaacagttg gagaaccact ggagatatag     780
atgacagttg gagtagcatg acttctcggg cagatatgaa cgacaaatgg gcatcttatg     840
ctggtcccgg tggatggaat gatcctgaca tgttggaggt gggaaatgga ggcatgacta     900
caacggaata tcgatcccat ttcagcattt gggcattagc aaaagcacct ctactgattg     960
gctgtgacat tcgatccatt gacggtgcga cttttccaact gttaagcaat gcggaagtta    1020
ttgcggttaa ccaagataaa cttggcgttc aagggaaaaa ggttaagact tacggagatt    1080
tggaggtgtg ggctggacct cttagtggaa agagagtagc tgtcgctttg tggaatagag    1140
gatcttccac ggctactatt accgcgtatt ggtccgacgt aggcctcccg tccacggcag    1200
tggttaatgc acgagactta tgggcgcatt caaccgaaaa atcagtcaaa ggacaaatct    1260
cagctgcagt agatgcccac gattcgaaaa tgtatgtcct aaccccacag tgattaacag    1320
gagaatgcag aagacaagtg atggttggct ctttcaagga tttgattacc ttaaagaatt    1380
tttcacatgt tatgaatcaa ttcaaagcaa ttatgtgttt tgaagagatt aagtcaataa    1440
```

```
at                                                                   1442

<210> SEQ ID NO 2
<211> LENGTH: 420
<212> TYPE: PRT
<213> ORGANISM: coffee arabica

<400> SEQUENCE: 2

Met Ala Ala Ala Tyr Tyr Leu Phe Ser Ser Lys Lys Ser His Gln
1               5                   10                  15

Lys Leu Val Leu Arg Ala Ser Leu Leu Met Phe Leu Cys Phe Leu Ala
                20                  25                  30

Val Glu Asn Val Gly Ala Ser Ala Arg Arg Met Val Lys Ser Pro Gly
            35                  40                  45

Thr Glu Asp Tyr Thr Arg Arg Ser Leu Leu Ala Asn Gly Leu Gly Leu
        50                  55                  60

Thr Pro Pro Met Gly Trp Asn Ser Trp Asn His Phe Ser Cys Asn Leu
65                  70                  75                  80

Asp Glu Lys Leu Ile Arg Glu Thr Ala Asp Ala Met Ala Ser Lys Gly
                85                  90                  95

Leu Ala Ala Leu Gly Tyr Lys Tyr Ile Asn Leu Asp Asp Cys Trp Ala
            100                 105                 110

Glu Leu Asn Arg Asp Ser Gln Gly Asn Leu Val Pro Lys Gly Ser Thr
        115                 120                 125

Phe Pro Ser Gly Ile Lys Ala Leu Ala Asp Tyr Val His Ser Lys Gly
    130                 135                 140

Leu Lys Leu Gly Ile Tyr Ser Asp Ala Gly Thr Gln Thr Cys Ser Lys
145                 150                 155                 160

Thr Met Pro Gly Ser Leu Gly His Glu Glu Gln Asp Ala Lys Thr Phe
                165                 170                 175

Ala Ser Trp Gly Val Asp Tyr Leu Lys Tyr Asp Asn Cys Asn Asp Asn
            180                 185                 190

Asn Ile Ser Pro Lys Glu Arg Tyr Pro Ile Met Ser Lys Ala Leu Leu
        195                 200                 205

Asn Ser Gly Arg Ser Ile Phe Phe Ser Leu Cys Glu Trp Gly Asp Glu
    210                 215                 220

Asp Pro Ala Thr Trp Ala Lys Glu Val Gly Asn Ser Trp Arg Thr Thr
225                 230                 235                 240

Gly Asp Ile Asp Asp Ser Trp Ser Ser Met Thr Ser Arg Ala Asp Met
                245                 250                 255

Asn Asp Lys Trp Ala Ser Tyr Ala Gly Pro Gly Gly Trp Asn Asp Pro
            260                 265                 270

Asp Met Leu Glu Val Gly Asn Gly Gly Met Thr Thr Thr Glu Tyr Arg
        275                 280                 285

Ser His Phe Ser Ile Trp Ala Leu Ala Lys Ala Pro Leu Leu Ile Gly
    290                 295                 300

Cys Asp Ile Arg Ser Ile Asp Gly Ala Thr Phe Gln Leu Leu Ser Asn
305                 310                 315                 320

Ala Glu Val Ile Ala Val Asn Gln Asp Lys Leu Gly Val Gln Gly Lys
                325                 330                 335

Lys Val Lys Thr Tyr Gly Asp Leu Glu Val Trp Ala Gly Pro Leu Ser
            340                 345                 350

Gly Lys Arg Val Ala Val Ala Leu Trp Asn Arg Gly Ser Ser Thr Ala
        355                 360                 365
```

```
Thr Ile Thr Ala Tyr Trp Ser Asp Val Gly Leu Pro Ser Thr Ala Val
        370                 375                 380

Val Asn Ala Arg Asp Leu Trp Ala His Ser Thr Glu Lys Ser Val Lys
385                 390                 395                 400

Gly Gln Ile Ser Ala Ala Val Asp Ala His Asp Ser Lys Met Tyr Val
                405                 410                 415

Leu Thr Pro Gln
        420
```

```
<210> SEQ ID NO 3
<211> LENGTH: 17
<212> TYPE: DNA
<213> ORGANISM: Artificial Sequence
<220> FEATURE:
<223> OTHER INFORMATION: Primer BETA1

<400> SEQUENCE: 3
atggtgaagt ctccagg                                                      17

<210> SEQ ID NO 4
<211> LENGTH: 17
<212> TYPE: DNA
<213> ORGANISM: Artificial Sequence
<220> FEATURE:
<223> OTHER INFORMATION: Primer BETA3

<400> SEQUENCE: 4
tcactgtggg gttagga                                                      17

<210> SEQ ID NO 5
<211> LENGTH: 23
<212> TYPE: DNA
<213> ORGANISM: Artificial Sequence
<220> FEATURE:
<223> OTHER INFORMATION: Primer BETA100

<400> SEQUENCE: 5
tgctccacaa agcagtggca att                                               23

<210> SEQ ID NO 6
<211> LENGTH: 23
<212> TYPE: DNA
<213> ORGANISM: Artificial Sequence
<220> FEATURE:
<223> OTHER INFORMATION: Primer BETA101

<400> SEQUENCE: 6
atttattgac ttaatctctt caa                                               23

<210> SEQ ID NO 7
<211> LENGTH: 35
<212> TYPE: DNA
<213> ORGANISM: Artificial Sequence
<220> FEATURE:
<223> OTHER INFORMATION: Primer 210-1

<400> SEQUENCE: 7
cggggtaccc cgcctctttt cttttggagt acaag                                  35

<210> SEQ ID NO 8
<211> LENGTH: 35
<212> TYPE: DNA
<213> ORGANISM: Artificial Sequence
<220> FEATURE:
```

<223> OTHER INFORMATION: Primer BAGUS2

<400> SEQUENCE: 8
cgcggatccg cgtctctgac aacagaggag agtgt    35

<210> SEQ ID NO 9
<211> LENGTH: 12
<212> TYPE: DNA
<213> ORGANISM: Artificial Sequence
<220> FEATURE:
<223> OTHER INFORMATION: KpnI

<400> SEQUENCE: 9
cggggtaccc cg    12

<210> SEQ ID NO 10
<211> LENGTH: 12
<212> TYPE: DNA
<213> ORGANISM: Artificial Sequence
<220> FEATURE:
<223> OTHER INFORMATION: BamHI

<400> SEQUENCE: 10
cgcggatccg cg    12

<210> SEQ ID NO 11
<211> LENGTH: 36
<212> TYPE: DNA
<213> ORGANISM: Artificial Sequence
<220> FEATURE:
<223> OTHER INFORMATION: Primer UP213-1

<400> SEQUENCE: 11
cggggtaccc cgacaaaaga ttgaacaata catgtc    36

<210> SEQ ID NO 12
<211> LENGTH: 35
<212> TYPE: DNA
<213> ORGANISM: Artificial Sequence
<220> FEATURE:
<223> OTHER INFORMATION: Primer TNOS1

<400> SEQUENCE: 12
cgcggatccg cggagctcga atttccccga tcgtt    35

<210> SEQ ID NO 13
<211> LENGTH: 35
<212> TYPE: DNA
<213> ORGANISM: Artificial Sequence
<220> FEATURE:
<223> OTHER INFORMATION: Primer TNOS2

<400> SEQUENCE: 13
cggggtaccc cggaattccc gatctagtaa catag    35

<210> SEQ ID NO 14
<211> LENGTH: 35
<212> TYPE: DNA
<213> ORGANISM: Artificial Sequence
<220> FEATURE:
<223> OTHER INFORMATION: Primer BETA100BI

<400> SEQUENCE: 14
cgcggatccg cgtgctccac aaagcagtgg caatt    35

<210> SEQ ID NO 15
<211> LENGTH: 35
<212> TYPE: DNA
<213> ORGANISM: Artificial Sequence
<220> FEATURE:
<223> OTHER INFORMATION: Primer BETA101BI

<400> SEQUENCE: 15
cgcggatccg cgatttattg acttaatctc ttcaa         35

<210> SEQ ID NO 16
<211> LENGTH: 35
<212> TYPE: DNA
<213> ORGANISM: Artificial Sequence
<220> FEATURE:
<223> OTHER INFORMATION: Primer UPSAL1

<400> SEQUENCE: 16
cacgcgtcga cgctccaccg cggtggcggc cgctc         35

<210> SEQ ID NO 17
<211> LENGTH: 23
<212> TYPE: DNA
<213> ORGANISM: Artificial Sequence
<220> FEATURE:
<223> OTHER INFORMATION: Primer UPSAL2

<400> SEQUENCE: 17
gggccccccc tcgaggtcga cgg         23

<210> SEQ ID NO 18
<211> LENGTH: 23
<212> TYPE: DNA
<213> ORGANISM: Artificial Sequence
<220> FEATURE:
<223> OTHER INFORMATION: Primer SO11

<400> SEQUENCE: 18
ttcttttgtt cctcggctgt ttg         23

<210> SEQ ID NO 19
<211> LENGTH: 24
<212> TYPE: DNA
<213> ORGANISM: Artificial Sequence
<220> FEATURE:
<223> OTHER INFORMATION: Primer SO2-1

<400> SEQUENCE: 19
ccaaacatca aacttctcgc aatc         24

<210> SEQ ID NO 20
<211> LENGTH: 27
<212> TYPE: DNA
<213> ORGANISM: Artificial Sequence
<220> FEATURE:
<223> OTHER INFORMATION: Primer BETA11

<400> SEQUENCE: 20
atggccgctg cttattacta ccttttt         27

<210> SEQ ID NO 21
<211> LENGTH: 27
<212> TYPE: DNA
<213> ORGANISM: Artificial Sequence
<220> FEATURE:
<223> OTHER INFORMATION: Primer BETA33

-continued

```
<400> SEQUENCE: 21
tcactgtggg gttaggacat acatttt                                          27
```